(12) United States Patent
Singh

(10) Patent No.: US 10,082,384 B1
(45) Date of Patent: Sep. 25, 2018

(54) SYSTEMS AND METHODS FOR DETECTING FIXATION FRAME PARAMETERS

(71) Applicant: Stryker European Holdings I, LLC, Kalamazoo, MI (US)

(72) Inventor: Manoj Kumar Singh, Mahwah, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 212 days.

(21) Appl. No.: 14/934,508

(22) Filed: Nov. 6, 2015

Related U.S. Application Data

(60) Provisional application No. 62/216,679, filed on Sep. 10, 2015.

(51) Int. Cl.
| | |
|---|---|
| *G01B 11/02* | (2006.01) |
| *A61B 17/62* | (2006.01) |
| *A61B 19/00* | (2006.01) |

(52) U.S. Cl.
CPC .............. *G01B 11/02* (2013.01); *A61B 17/62* (2013.01); *A61B 19/50* (2013.01); *A61B 2019/502* (2013.01)

(58) Field of Classification Search
CPC ..................................................... G01B 11/02
See application file for complete search history.

(56) References Cited

U.S. PATENT DOCUMENTS

| | | |
|---|---|---|
| 4,365,624 A | 12/1982 | Jaquet |
| 4,615,338 A | 10/1986 | Ilizarov et al. |
| 4,978,348 A | 12/1990 | Ilizarov |
| 5,546,942 A | 8/1996 | Zhang |
| 5,681,309 A | 10/1997 | Ross, Jr. et al. |
| 5,702,389 A | 12/1997 | Taylor et al. |

(Continued)

FOREIGN PATENT DOCUMENTS

| | | |
|---|---|---|
| DE | 102006048451 A1 | 4/2008 |
| WO | 2015024600 A1 | 2/2015 |

OTHER PUBLICATIONS

U.S. Appl. No. 14/523,150, filed on Oct. 24, 2014, Methods and Systems for Adjusting an External Fixation Frame.

(Continued)

*Primary Examiner* — Manuel A Rivera Vargas
(74) *Attorney, Agent, or Firm* — Lerner, David, Littenberg, Krumholz & Mentlik, LLP

(57) ABSTRACT

A detection device, such as a camera-enabled smart phone, may be used to take one or more pictures of an external fixation frame attached to a patient. The pictures may be transmitted to a computer system accessible by the patient's physician. The computer system may uniquely identify each strut of the external fixation frame and determine the length of each strut. The computer system may compare the determined length of each strut to a planned length of the struts for a particular time interval as outlined in a correction plan. If the struts are the correct length for the particular time interval, the fact may be indicated to the physician and transmitted to the patient. If the struts are not the correct length, the computer system may update the correction plan to account for the discrepancy plan, with the updated correction plan transmitted to the patient.

18 Claims, 5 Drawing Sheets

(56) References Cited

U.S. PATENT DOCUMENTS

| | | |
|---|---|---|
| 5,728,095 A | 3/1998 | Taylor et al. |
| 5,824,085 A | 10/1998 | Sahay et al. |
| 5,880,976 A | 3/1999 | DiGioia, III et al. |
| 5,971,984 A | 10/1999 | Taylor et al. |
| 6,030,386 A | 2/2000 | Taylor et al. |
| 6,129,727 A | 10/2000 | Austin et al. |
| 6,205,411 B1 | 3/2001 | DiGioia, III et al. |
| 6,701,117 B2 | 3/2004 | Kaji |
| 6,701,174 B1 | 3/2004 | Krause et al. |
| 6,711,432 B1 | 3/2004 | Krause et al. |
| 7,039,225 B2 | 5/2006 | Tanaka et al. |
| 7,280,683 B2 | 10/2007 | Bi et al. |
| 7,388,972 B2 | 6/2008 | Kitson |
| 7,394,946 B2 | 7/2008 | Dewaele |
| 7,547,307 B2 | 6/2009 | Carson et al. |
| RE40,914 E | 9/2009 | Taylor et al. |
| 7,837,621 B2 | 11/2010 | Krause et al. |
| 7,876,942 B2 | 1/2011 | Gilboa |
| 8,055,487 B2 | 11/2011 | James |
| 8,157,800 B2 | 4/2012 | Vvedensky et al. |
| 8,257,353 B2 | 9/2012 | Wong et al. |
| 8,419,732 B2 | 4/2013 | Mullaney |
| 8,654,150 B2 | 2/2014 | Haskell |
| 8,777,946 B2 | 7/2014 | Lindahl et al. |
| 8,864,750 B2 | 10/2014 | Ross et al. |
| 8,952,986 B2 | 2/2015 | Haskell |
| 9,129,054 B2 | 9/2015 | Nawana et al. |
| 2002/0010465 A1 | 1/2002 | Koo et al. |
| 2003/0191466 A1 | 10/2003 | Austin et al. |
| 2004/0039259 A1 | 2/2004 | Krause et al. |
| 2004/0068187 A1 | 4/2004 | Krause et al. |
| 2004/0073211 A1 | 4/2004 | Austin et al. |
| 2004/0073212 A1 | 4/2004 | Kim |
| 2005/0054917 A1 | 3/2005 | Kitson |
| 2005/0215997 A1 | 9/2005 | Austin et al. |
| 2006/0276786 A1 | 12/2006 | Brinker |
| 2008/0234554 A1 | 9/2008 | Vvedensky et al. |
| 2008/0319448 A1 | 12/2008 | Lavallee et al. |
| 2010/0087819 A1 | 4/2010 | Mullaney |
| 2010/0286995 A1 | 11/2010 | Pekar et al. |
| 2011/0004199 A1 | 1/2011 | Ross et al. |
| 2011/0313418 A1 | 12/2011 | Nikonovas |
| 2012/0330312 A1* | 12/2012 | Burgherr ............... A61B 17/62 606/54 |
| 2014/0063220 A1 | 3/2014 | Taylor |
| 2014/0081659 A1 | 3/2014 | Nawana et al. |
| 2014/0236153 A1 | 8/2014 | Edelhauser |
| 2015/0261922 A1 | 9/2015 | Nawana et al. |
| 2015/0282796 A1 | 10/2015 | Nawana et al. |
| 2016/0092651 A1* | 3/2016 | Austin ................. G06Q 50/24 705/2 |

OTHER PUBLICATIONS

Screenshots from Taylor Spatial Frame iAdjust Surgeon Training 6 HD YouTube Video Published Mar. 24, 2015.

\* cited by examiner

SYSTEMS AND METHODS FOR DETECTING FIXATION FRAME PARAMETERS

CROSS-REFERENCE TO RELATED APPLICATIONS

This application claims the benefit of the filing date of U.S. Provisional Patent Application No. 62/216,679 filed Sep. 10, 2015, the disclosure of which is hereby incorporated herein by reference.

BACKGROUND OF THE DISCLOSURE

The present disclosure relates to systems and methods for detecting fixation frame parameters. More particularly, the present disclosure relates to systems and methods that facilitate medical personnel in determining whether, and the extent to which, a fixation frame adjustment is proceeding according to a correction schedule.

The external fixation market may be generally divided into two segments: acute trauma and reconstructive. The trauma segment may include modular fixators, which may be characterized by limited componentry and rapid application. Consequently, they are known for being fairly simple products. Many of these frames are used for temporizing fixation and may only be on the patient for hours or days. The reconstructive segment generally leans toward ring fixation. Examples of ring fixators are shown in U.S. Pat. Nos. 4,365,624, 4,615,338, 4,978,348, 5,702,389, and 5,971,984. Their use of a combination of pins and wires to achieve a variety of polyaxial pin/wire attachments may provide stability. They can accomplish a full six degrees of freedom and can correct primary deformities without creating secondary deformities.

It is sometimes necessary to realign, reposition and/or securely hold two bone elements relative to one another. For example, in the practice of medicine, bone fragments and the like sometimes are aligned or realigned and repositioned to restore boney continuity and skeletal function. At times, this may be accomplished by sudden maneuver, sometimes followed by skeletal stabilization with cast, plate and screws, intramedullary devices, or external skeletal fixators.

A bone fragment can be moved, in general, from its original position as in a nonunion or malunion or from its intended position as in congenital deformities along six separate movements or degrees of freedom, a combination of three orthogonal translational axes (e.g., typical "X," "Y" and "Z" axes) and three orthogonal rotational axes (e.g., rotation about such typical "X," "Y" and "Z" axes).

External fixation devices may be attached to the boney skeleton with threaded and/or smooth pins and/or threaded and/or smooth and/or beaded wires. Such constructs are commonly referred to as orthopaedic external fixators or external skeletal fixators. External fixators may be utilized to treat acute fractures of the skeleton, soft tissue injuries, delayed union of the skeleton when bones are slow to heal, nonunion of the skeleton when bones have not healed, malunion whereby broken or fractures bones have healed in a malposition, congenital deformities whereby bones develop a malposition, and bone lengthening, widening, or twisting.

A circumferential external fixator system was disclosed by G. A. Ilizarov during the early 1950s. The Ilizarov system includes at least two rings or "halos" that encircle a patient's body member (e.g., a patient's leg), connecting rods extending between the two rings, transfixation pins that extend through the patient's boney structure, and connectors for connecting the transfixation pins to the rings.

Often orthopaedic external fixators such as Ilizarov fixators must be repositioned after their initial application. Such modification may be necessary to convert from one correctional axis to another or to convert from an initial adjustment type of fixator to a weight bearing type of fixator, some of the correctional configurations not being stable enough for weight bearing.

External fixators may be adjusted over a period of time to reposition bone segments. The adjustment of the external fixation may be implemented according to a "prescription" or correction plan. Physicians may adjust the external fixator at precise times over a period of time (e.g, on a daily basis for three weeks). Patients, however, may not desire to visit the physician's office every time an adjustment is needed. For this reason, many external fixators can be adjusted by the patients themselves without the assistance of a physician. The adjustment of the external fixator should nonetheless strictly comply with the predetermined correction plan. In some occasions, patients may not adjust their own external fixator according to the correction plan for a variety of reasons. For instance, patients may not understand how to use the external fixator correctly. In addition, when the patients themselves adjust the external fixators, physicians may not even know whether patients are in fact adjusting the external fixators according to the correction plan. For the foregoing reasons, it is desirable to provide systems and methods to detect fixation frame parameters to allow determination of whether the adjustment is proceeding according to plan.

BRIEF SUMMARY OF THE INVENTION

According to one embodiment of the disclosure, a computer system includes at least one processor configured to execute instructions to receive a plurality of images of an external fixation system coupled to a patient, each image containing at least one strut of the external fixation system. The processor is further configured to determine a length of the at least one strut in each image, identify the at least one strut in each image corresponding to a predefined correction plan for the at least one strut in each image, and compare the determined length of the at least one strut in each image to a planned strut length of the predefined correction plan, the planned strut lengths being stored in memory of the computer system. The processor may also analyze whether an updated correction plan should be created based on the determined length of each the at least one strut in each image, and transmit information from the analysis for adjusting the struts of the external fixation system. The instructions to identify the at least one strut in each image may include comparing visual indicia, such as a quick response (QR) code on the at least one strut to corresponding indicia stored in the memory. The planned strut lengths stored in memory may include a length component and a time-interval component. The at least one processor may further be configured to execute instructions to receive a time indicator corresponding to each of the plurality of images. The instructions to compare the determined length of each of the plurality of struts to the planned strut length may further include comparing the time indicator corresponding to each of the plurality of images to a time-interval component of the planned strut length.

According to a further embodiment of the disclosure, a computer system including at least one processor configured to execute instructions to receive a plurality of images of an external fixation system coupled to a patient, each image containing at least one strut of the external fixation system, and determine a length and an identity of the at least one strut in each image. The processor may further compare the determined length of each of the plurality of struts to a corresponding planned strut length, the corresponding planned strut lengths being stored in memory of the computer system, and transmit information indicative of whether the determined length of each of the plurality of struts substantially matches the corresponding planned strut length. The instructions to determine the identity of the at least one strut in each image may include comparing visual indicia, such as a quick response (QR) code, on the at least one strut to corresponding indicia stored in the memory. The corresponding planned strut lengths stored in memory may include a length component and a time-interval component. The at least one processor may further be configured to execute instructions to receive a time indicator corresponding to each of the plurality of images. The instructions to compare the determined length of each of the plurality of struts to a corresponding planned strut length may further include comparing the time indicator corresponding to each of the plurality of images to a time-interval component of the planned strut lengths.

According to yet another embodiment of the disclosure, a computer system includes at least one processor configured to execute instructions to determine a predefined correction for an external fixation system including a plurality of adjustable length struts, the predefined correction plan including for each of the plurality of adjustable length struts an original length and a final length. The processor may further be configured to receive a plurality of images of the external fixation system coupled to a patient, each image containing at least one strut of the external fixation system, and determine a length of the at least one strut in each image. The processor may also be configured to execute instructions to identify the at least one strut in each image corresponding to a time-interval in the predefined correction plan for the at least one strut in each image, and compare the determined length of the at least one strut in each image to a planned strut length at the time-interval in the predefined correction plan, the planned strut lengths being stored in memory of the computer system. Still further, the processor may be configured to execute instructions to determine whether an updated correction plan should be created based on the determined length of each the at least one strut in each image. The instructions to identify the at least one strut in each image may comprise comparing visual indicia, such as a quick response (QR) code, on the at least one strut to corresponding indicia stored in the memory. The planned strut lengths stored in memory may include a length component. The at least one processor may be further configured to execute instructions to receive a time indicator corresponding to each of the plurality of images. The instructions to compare the determined length of each of the plurality of struts to the planned strut length may further include comparing the time indicator corresponding to each of the plurality of images to the time-interval component of the planned strut length.

BRIEF DESCRIPTION OF THE DRAWINGS

Various embodiments of the present invention will now be described with reference to the appended drawings. It is appreciated that these drawings depict only some embodiments of the invention and are therefore not to be considered limiting of its scope.

DETAILED DESCRIPTION

Figure 1:
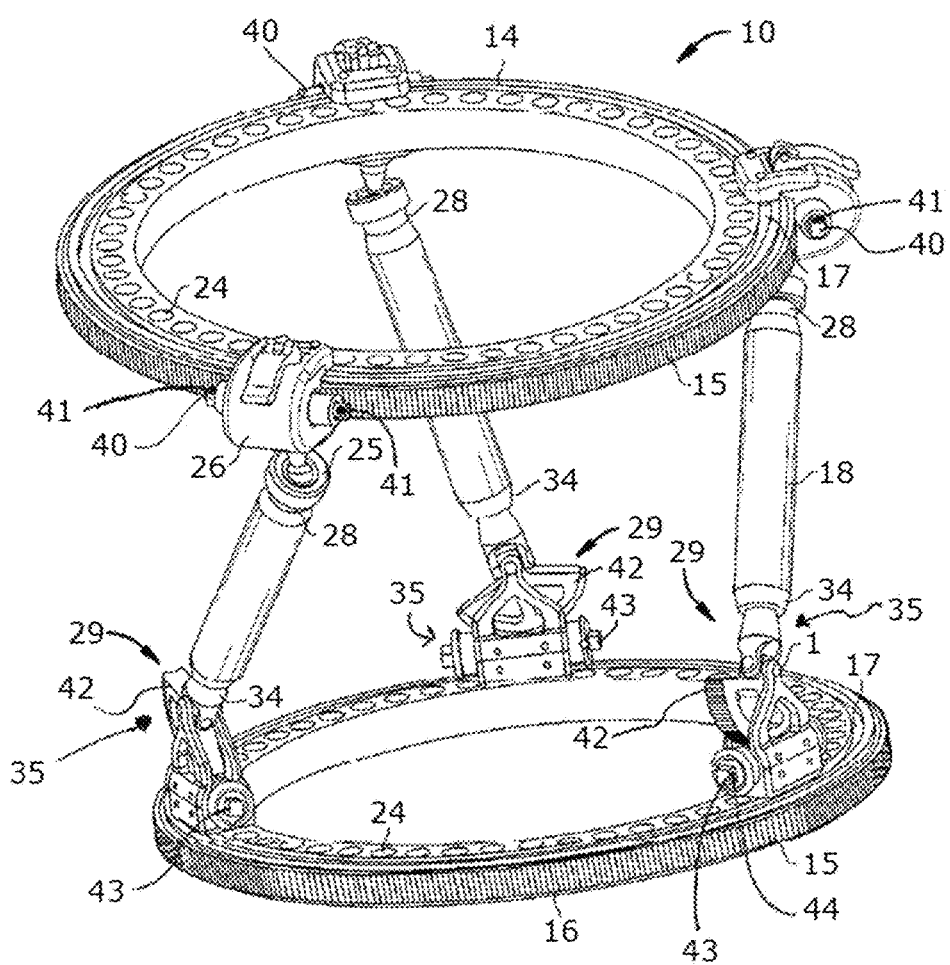
FIG. 1 is an isometric view of an external fixation frame.

FIG. 1 illustrates one example of an external fixation frame 10 that may be used in connection with the systems and methods of this disclosure. As it will become clear, other types of external fixation frames may be used in conjunction with the systems and methods of this disclosure in similar manners. External fixation frame 10 is briefly described below to provide context for the systems and methods for determining parameters of fixation frames disclosed herein.

As seen in FIG. 1, external fixation frame 10 may be utilized with any long bone, in particular, the tibia and the femur, and includes a first ring 14 and a second ring 16. In some embodiments, both rings 14, 16 are identical. Each ring 14 includes a worm gear 15 formed around its outer circumference. Two grooves 17 are formed in the upper and lower surfaces of ring 14 around its circumference adjacent the worm gear 15. Ring 14 (or 16) may include a multi-level configuration with the upper and lower surfaces having alternate steps including through holes 24. In certain embodiments, rings 14, 16 are connected by three variable length struts 18. The three struts 18 have first ends 28 mounted to the first ring 14 via a connector 25 coupled to a sliding or shuttle unit 26, which is circumferentially moveable around ring 14. In several embodiments, the first ends 28 are connected to sliding or shuttle units 26 by a connector 25 having a ball or spherical joint. As is typical, the rings 14 and 16 are connected to a bone (e.g., tibia) by a plurality of bone pins or wires (not shown). In some embodiments, the pins or wires are connected to each ring 14, 16 by connection elements, which are located in one or more of a multiplicity of holes 24 around the circumference of the first and second rings 14 and 16. Although holes 24 are shown, any structure which locates the pins or wires with respect to the circumference of rings 14 and 16 can be utilized. Lower ends 34 of struts 18 are connected to lower ring 16 by standard universal-joints 35, which allow free rotation about only two axes rather than the three axes of the spherical joint at the first strut end 28.

Ring 14 may be coupled to a first bone element via pins or wires and, similarly, ring 16 is coupled to a second bone element by similar pins or wires. Shuttle units 26 are slidable about ring 14 in a track and are preferably driven by a driver that interacts with shuttle units 26. Each shuttle unit 26 may include a worm or screw 40 configured to mesh with worm gear 15 of first ring 14.

Identification tags 41, such as RFID tags, may be disposed on both sides of each screw 40. Each identification tag 41 stores identification data and is adapted to generate a signal indicative of the identification data of a particular screw 40. For instance, the identification data may include a number or letter assigned to a specific screw 40. A signal reader on the driver may be adapted to read the signals generated from each identification tag 41 to identify the screw 40 associated with a particular identification tag 41. In operation, rotation of screw 40 causes shuttle unit 26 to slide about ring 14, thus changing the position of strut 18. A second connector 29 between strut 18 and second lower ring 16 has a standard universal joint 35, which allows the strut to rotate freely about two axes, which may be oriented perpendicular to each other. Each universal joint 35 may include a gear portion 42 and screw 43. Screw 43 is adapted to engage gear portion 42 and may be rotated by driver 126.

During operation, rotation of screw 43 causes gear portion 42 to pivot about a pin 1, thereby causing strut 18 to change its orientation relative to the rings 14 and 16. Thus, each of the three sliding shuttle units 26 may be independently controlled and the three connectors 29 at the second ring 16 may be independently controlled so that the ring 14, and therefore the bone element attached to ring 14, can be positioned in proper alignment with ring 16 and the bone element attached to ring 16. Rings 14 and 16 can be repositioned after their initial alignment as desired by the surgeon.

Figure 2A:
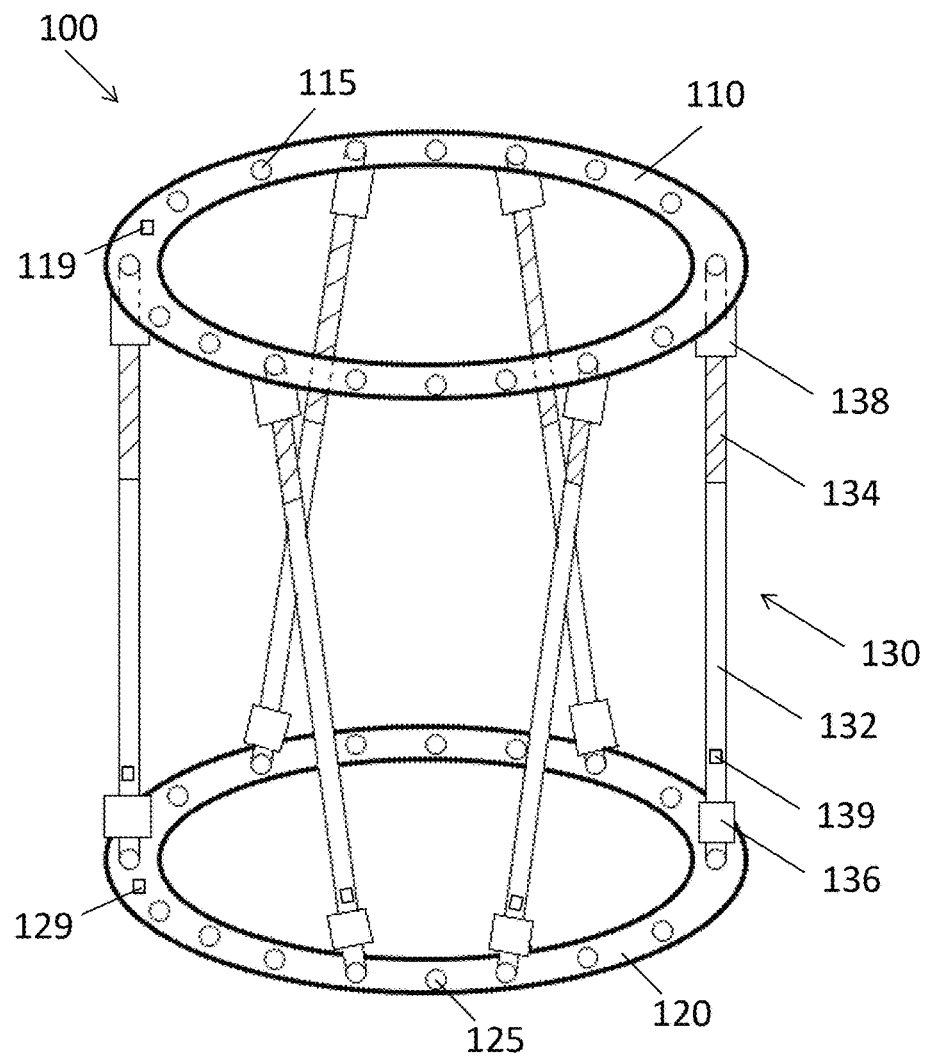
FIG. 2A is a schematic representation of another external fixation frame.

Still other types of external fixation frames may provide adequate deformity correction and may be used with the systems and methods described in greater detail below. For example, FIG. 2A illustrates another external fixation frame 100. Fixation frame 100 generally includes a first ring 110 with a plurality of through-holes 115 and a second ring 120 with a plurality of through-holes 125. Six telescopic struts 130 couple the first ring 110 to the second ring 120. For example, each strut 130 may include a generally cylindrical member 132 and a threaded shaft 134 that may thread into or out of cylindrical member 132 to increase or decrease the length of the strut 130 in a telescoping fashion. Cylindrical member 132 may be coupled to second ring 120 via a through-hole 125, and a joint 136 may be provided near or at the end of cylindrical member 132 to provide for jointed movement of cylindrical member 132 with respect to second ring 120. Similarly, threaded member 134 may be coupled to first ring 110r via a through-hole 125, and a joint 138 may be provided near or at the end of threaded member 135 to provide for jointed movement of threaded member 134 with respect to first ring 110. Joints 136 and 138 may be any suitable joint including, for example, a universal joint or a polyaxial ball-and-socket type joint, and it should be understood that joints 136 and 138 do not need to be the same type of joint as one another.

As a user changes the length of struts 130, for example by engaging a screwdriver or motorized tool with a head of the threaded member 134 and rotating the threaded member, rings 110 and 120 change position with respect to one another due to the change in length of the struts 130 and the corresponding movement provided by joints 136 and/or 138. The bones connected to first ring 110, and second ring 120, respectively, generally move in sync with the rings to which they are attached. Generally, fixation frame 100 has a similar function as fixation frame 10, still other embodiments of fixation frames have similar functionality. For example, some fixation frames also have two rings and six struts, but the end of each strut is coupled to the end of an adjacent strut, such that there are only three points of connection between the struts and each ring, as opposed to the six shown in FIG. 2A.

Once fixation frame 100 is attached to a patient, the patient may be provided with a correction schedule that details how each strut 130 should be adjusted so that rings 110 and 120 move with respect to one another to correct the bone deformity. The correction schedule may instruct the patient to adjust each strut 130 one or more times per day for the course of days and/or weeks. In one example, the patient may be provided with a handheld driver that engages with a portion of strut 130 to increase or decrease the length of the strut by rotating the strut. The driver and/or struts 130 may be provided with a feature that effectively discretizes the rotation of the strut 130 into equal increments, for example each rotation may be discretized to an eighth of a turn or a quarter turn, corresponding to a particular change in length of the strut, such as 1 mm. One benefit of providing the user with a correction schedule and a driver that discretely changes in length of the struts 130 is that the patient may be able to adjust the fixation frame 100 himself at home, without needing to repeatedly visit his or her physician each time an adjustment is to take place. However, one potential drawback is that the lack of physician supervision may increase the likelihood of the patient performing incorrect adjustments on the fixation frame 100. One way to protect against this drawback is for the patient to visit his or her physician at some interval, for example every few days, to allow the physician to ascertain whether the correction is proceeding according to plan and/or whether or not changes to the correction plan should be made. This may provide a suitable compromise between the patient's freedom to adjust the fixation frame 100 without having to visit his physician for each adjustment, while helping avoid patient adjustment error by having periodic checkups with the physician during the course of the adjustment.

Figure 3:
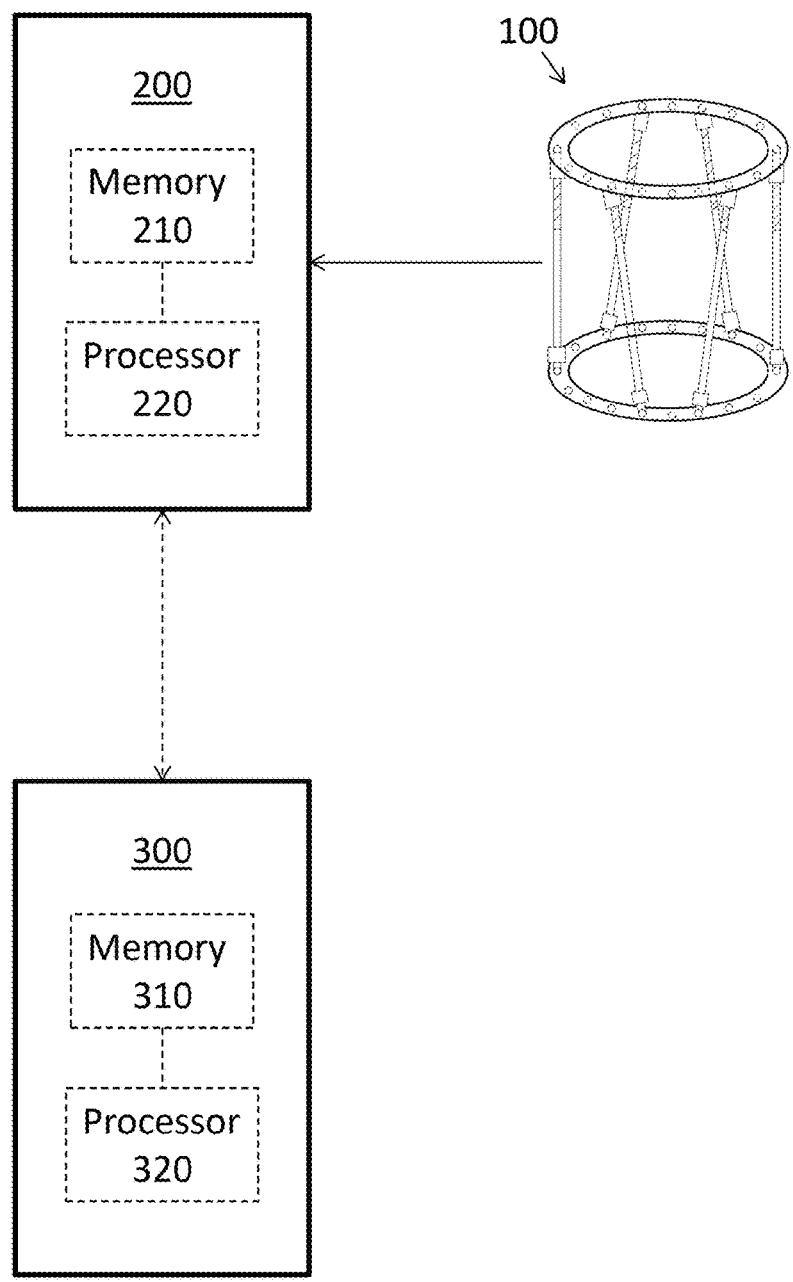
FIG. 3 is a schematic representation of a detection device and a computer system according to an aspect of the disclosure.

It may be beneficial to provide systems and methods that allow for a physician to assess the status of the deformity correction without requiring the patient to visit the physician. This may minimize the necessity for the patient to make frequent trips to the physician while still maintaining the ability of the physician to determine if the deformity correction is progressing according to plan and/or in a desired fashion. One such system and method may include a detection device capable of transmitting information to a physician's computer. For example, as shown in FIG. 3, a detection device 200 may include memory 210 and a processor 220. In one embodiment, detection device 200 may be a handheld device that is operatively coupled to a camera, such as a typical smart phone. The detection device 200 may be in communication with a computer system 300 having a memory 310 and processor 320, for example vie a wireless or wired connection. Generally, a patient or a caretaker or other person may use detection device 200 to determine particular parameters of fixation frame in a given state.

One aspect of the present disclosure is described below for the example in which the detection device 200 is a camera-enabled smart phone. After fixation frame 100 has been attached to a patient, the patient is sent home with a correction schedule indicating how each strut 130 should be adjusted at predetermined time intervals. Following adjustment of the struts 130 of the fixation frame 100 for a certain number of intervals, the patient may use detection device 200 to provide information to the physician so that the physician may determine whether the correction is proceeding in a desired fashion according to a predetermined or prescribed plan, for example. To accomplish this, the user or another person may use the detection device 200 to take one or more pictures of fixation frame 100. The picture(s) may be stored in memory 210 and accessed by an application and/or processor 220 to analyze the picture(s). Preferably, each picture includes a time identifier, e.g. a time stamp, to identify the time and date the picture was taken. In one example, each strut 130 includes visual indicia 139 unique with respect to each other strut 130. For example, the visual indicia 139 of each strut 130 may be a barcode, a quick-response code, a numeric or alphabetic code, a color, a shape, or any combination of the above. Preferably, the unique codes are stored in memory 210 so that the application and/or processor 220 on the device 200 is able to compare the stored codes with the codes captured in the image to uniquely identify each strut 130. Depending on the position and orientation of each strut 130, multiple pictures may be necessary to capture all the desired information for each strut. Each ring 110, 120, may also include an identifier 119, 129 to distinguish between the rings, similar to that described above in connection with the struts 130. Further, the rings 110, 120 may each include separate visual indicia to facilitate the unique identification of the through-holes of each ring in relation to the other through-holes of the same ring. If rings 110, 120, have visual indicia 119, 129 uniquely identifying the rings, the indicia may also be used to identify the through-holes 115, 125 of each ring.

After the picture is taken, the size and identification of each strut 130 may be determined automatically or semi-automatically. For example, the application and/or processor 220 on the device 200 may compare the visible visual indicia on each strut 130 in each picture to information stored in memory 210 corresponding to the visual indicia 139 to determine the identity of the strut(s) 130 visible in the picture. The application and/or memory 210 may be preloaded with this information, and/or the physician or patient may enter such information into memory 210 after the fixation frame 100 is attached to the patient. For each strut identified by the device 200, a length may be calculated and then associated to the unique strut and a specific time. For example, because each strut 130 may have a fixed length for the cylindrical member 132, the device 200 may use the known length of the cylindrical member 132 of the identified strut 130 to calibrate an image element, such as a pixel, to a particular distance. Based on this, the device 200 may determine the total length of the identified strut 130. This process may be repeated for each strut 130 based on as many pictures as are necessary to identify and measure each unique strut 130. Once a length of each strut 130 has been determined, the information may be stored in memory 210, preferably with a corresponding time indicator that correlates the identified strut 130 lengths to a particular time.

Figure 2B:
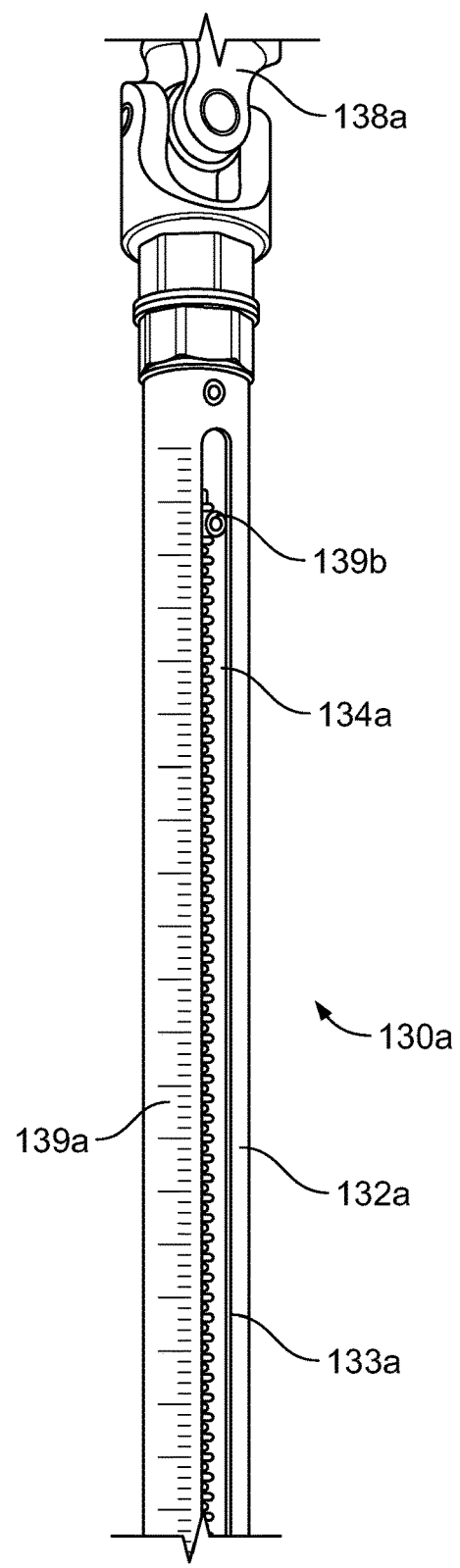
FIG. 2B is perspective view of an alternate embodiment of a strut of an external fixation frame.

Another example of a strut 130a is illustrated in FIG. 2B. Strut 130a may include a cylindrical member 132a similar to cylindrical member 132, with an elongated slot 133a extending along at least a portion of the length of cylindrical member 132a. A portion of threaded member 134a may be visible through elongated slot 133a. Cylindrical member 132a may include visual indicia 139a in the form of hash lines similar to those on a ruler to indicate distance. Similarly, threaded member 134a may include an indicium 139b in the form of a structure, such as a protrusion, that remains in slot 133a as threaded member 134a threads into or out of cylindrical member 132a. Similar to the method described above, a picture of strut 130a may be analyzed to determine the length of strut 130a at the time the picture is taken. In one example, the indicium 139b may be recognized and its position in relation to indicia 139a may be analyzed to determine the length of strut 130a. In another example, the distance between indicium 139b and an end of slot 133a may be analyzed to determine the length of strut 130a.

The device 200 may also determine other relevant information from images stored in memory 210. For example, if the first and second rings 110, 120 include unique identifiers, device 200 may differentiate which ring is the top ring 110 and which ring is the bottom ring 120. Further, the identifier may include information regarding the specific type of rings 110, 120, including for example the size (e.g. diameter and/or thickness) and shape of the rings, as well as the number and location of the through-holes 115, 125 of the rings. This information may facilitate device 200 in calibrating a picture being analyzed. For example, a known thickness and/or diameter of a ring in the picture may help determine the scale of the fixation frame 100 in the image. Still further, if the rings 110, 120 include one or more identifiers to differentiate the positioning of the through-holes 115, 125, device 200 may use that information to identify each through-hole. For example, ring 110 is illustrated as a circular ring with substantially identical through-holes 115 positioned at substantially equal distances around the circumference of the ring 110. An identifier on ring 110 may facilitate device 200 in differentiating among the otherwise substantially identical through-holes 115. This information may facilitate device 200 in determining which through-holes 115, 125 a particular strut 130 is connected to, if such information is desired.

In some embodiments, at least some of the information described above may be manually input into device 200 by a user. For example, an application on device 200 may display each image acquired by the patient and request the patient to identify, for example via a touch-screen interface, which ring is the top ring 110, which ring is the bottom ring 120, the identity of each strut 130, and/or the identity of a through-hole 115, 125. Still further, the device 200 may present information, such the identity of each strut 130 in a particular image, to the user so that the user may confirm that the identification is accurate. Still further, with respect to any static information, such as the type, size, and shape of rings 110, 120, such information may be input into memory 210 and/or the application on device 200 after external fixation frame 100 is attached to the patient.

With the identity and length of each strut 130 determined by device 200, the information may be stored in memory 210 and transmitted to computer system 300, for example via a wireless connection. If computer system 300 is a physician or other medical personnel computer, the transmitted information preferably includes some type of patient or case identifier so that computer system 300 is able to access the case file of the patient transmitting the information. The strut identity and length information received by computer system 300 may be compared, manually or automatically, to a correction schedule corresponding to the patient. In one example, the transmitted information includes an indication of the time the image was taken, so that the computer 300 may determine the relevant point in the correction schedule that is to be used for comparison. The correction schedule may include an intended length for each strut 130 after each prescribe adjustment event. Based on the time information corresponding to the determined strut length, computer system 300 may access memory 310 in which the correction schedule is stored and utilize processor 320 to compare the intended strut length for a particular time in the correction schedule to the determined strut length for that time period, and for each strut determine the difference between the intended strut length and the determined strut length.

A separate application or a copy of the same application may be included on computer system 300 to assist the physician in making use of the comparison of the intended length of each strut 130 to the determined strut length. For example, after the application and/or processor 320 compares the determined lengths of struts 130 to the intended lengths, the application and/or processor 320 may cause a simple display to appear indicating that the determined length of each strut 130 matches the intended length of each strut for the given correction interval. Preferably, each the intended length of each strut 130 is displayed next to the determined length of each strut 130, along with an indication of whether the determined length is suitable in light of the intended length. To the extent any discrepancy is found between the intended length of each strut 130 and the determined lengths, that discrepancy may also be displayed. The application and/or memory 210 may include a particular value for an acceptable buffer between the intended length and determined length of each strut 130. For example, the application and/or processor 320 may only indicate a problematic deviation if the determined length of a strut 130 is more than 5% greater or less than the intended length 130 for the relevant interval of the correction schedule. In another example, the threshold for problematic deviation may be between about 1% to about 2% in either direction.

Upon being presented with a discrepancy between the intended length and determined length of one or more struts 130, the physician may undertake a number of different corrective actions. For example, for a relatively simple error, the physician may understand, with or without aid of computer system 300, that one strut 130 or particular struts 130 need to have minor adjustments to bring the actual length of the struts 130 into conformance with the intended lengths for a particular correction schedule interview. The physician may provide this information to the patient and/or the patient's caretaker in any desirable fashion, including via communication between computer system 300 and detection device 200. In some examples, computer system 300 may display or otherwise indicate how the length of each strut 130 needs to be changed in order to bring the actual lengths of struts 130 into conformance with the intended lengths. In some examples, this information may be provided to the patient or patient's caretaker in any desired fashion. In other examples, the physician may determine that a new correction schedule should be created. For example, if the patient failed to adjust lengths of struts 130, either intentionally or unintentionally, for a particular interval of the correction schedule, at least two options for rectification are possible.

In one option, the physician may transmit instructions to the patient, for example from computer system 300 to detection device 200, to perform the missed adjustment so that, going forward, the patient is proceeding according to the original schedule. In another option, the physician may determine it is better to continue according to the original schedule, time-shifted by the interval missed. For example, if each correction interval is one day, the physician may determine to extend the correction schedule by one day and otherwise continue the correction as possible. In this example, the physician may update the correction schedule, for example using computer system 300, and cause the updated correction schedule (which is time-shifted by one day) to be transmitted to the patient, for example via communication with detection device 200. The patient would continue the correction according to the updated correction schedule, ignoring the original schedule.

In order to update a correction schedule, for example using computer system 300, the physician may manually update the correction schedule, or the computer system 300 may suggest an updated schedule for the physician's review, which may be accepted by the physician and transmitted to the patient, discarded by the physician, or modified by the physician as desired. In all cases, computer system 300 may display an animation or other visual indication of how struts 130 would be corrected to provide visualization of the process.

Although the determination of lengths of struts 130 is described above as taking place on detection device 200 via processor 220, it should be understood that such determination may alternately occur on computer system 300 or any other computer system in communication with detection device 200 and/or computer system 300. Similarly, any other calculation or comparison described as being completed on detection device 200 or computer system 300 may be performed on either device or any other computer system in communication with detection device 200 and/or computer system 300. Preferably, the only exception is that any change in correction plan is performed on computer system 300 when controlled by an authorized physician.

Although the described example of a detection device 200 above is a smart phone with camera capability, detection device 200 may be any computer system with memory and a processor that may be interfaced with a camera, and the components need not be housed within a single structure. For example, detection device 200 may be a mobile tablet device or a laptop with an integrated camera, or a mobile tablet device or laptop capable of receiving a picture from a separate camera device.

Further, although described in relation to fixation frame 100 which includes two rings 110, 120, and six struts 130, the disclosure may apply to other types of fixation frames with adjustable length struts, including fixation frames with more or different types of rings, and more, fewer, and/or different types of adjustable length struts.

Figure 4:
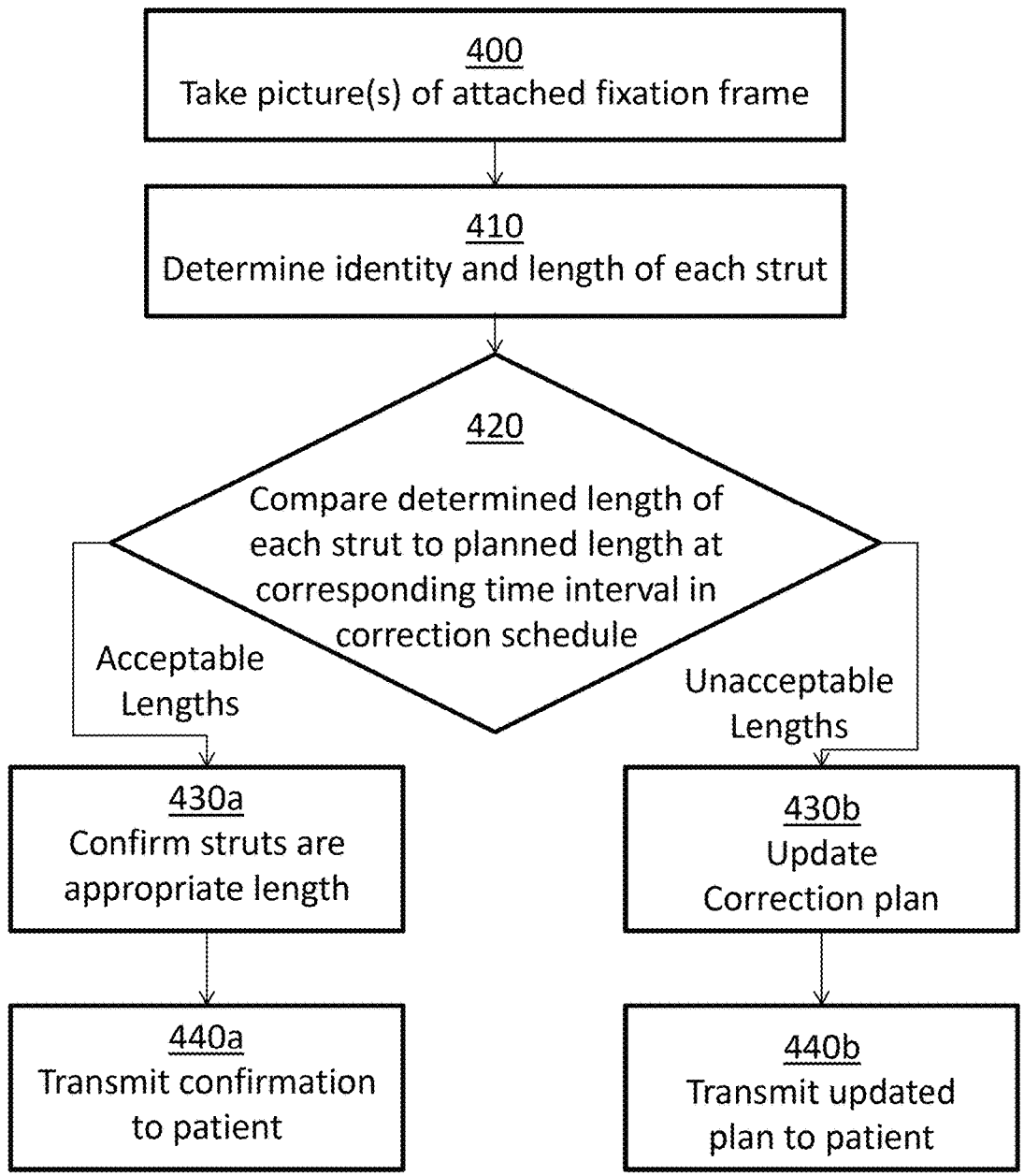
FIG. 4 is a flow chart illustrating a method according to an aspect of the disclosure.

FIG. 4 shows a flow chart summarizing the use of the present disclosure according to one aspect. For example, in step 400, one or more pictures are taken of fixation frame 100 after it has been attached to the patient. Preferably, the number of pictures is the minimum required to identify each strut 130 and determine the length of each strut. As noted above, the picture may be taken by a camera integral with detection device 200, or a separate camera. In step 410, the identity and length of each strut 130 is determined. Step 410 may be performed directly on detection device 200, whether the pictures were taken with an integral camera or a separate camera and the pictures later transmitted to the detection device. On the other hand, step 410 may be performed on computer system 300 whether the pictures are transmitted from detection device 200 to computer system 300 or from a separate camera to computer system 300. As noted above, step 410 may be assisted by comparing visual indicia on each strut 130 to visual indicia stored in memory accessible by the processor performing step 410, whether this is memory 210 and processor 220 or memory 310 and processor 320.

In step 420, the correction schedule stored in memory 210 or 310 is accessed by the processor 220 or 320 performing the step. As noted above, processor 320 preferably carried out step 420 so that the appropriate physician may review the results. The determined length of each strut for the time interval in which the picture was taken is compared to the planned length of the corresponding strut for the relevant time interval in the correction plan. If the determined strut lengths are acceptable compared to the planned strut lengths, the processor 320 may cause computer system 300 to indicate to the physician that the strut lengths are acceptable in step 430*a*, which information may be transmitted from computer system 300 to the patient, for example via the detection device 200 in step 440*a*, to inform the patient the fixation frame 100 is correctly adjusted for the given time interval. If the comparison of the determined strut lengths to planned strut lengths shows the struts have not been adjusted according to the correction plan, the physician may update the correction plan to account for the discrepancies. The update may be performed directly by the physician, the processor 320 may provide a suggested update for the physician to accept, or the processor 320 may automatically update the correction plan, in step 430b. Once updated, the plan may be transmitted to the patient in step 440b, for example via the detection device 200. It should be understood that this process may be repeated as many times as desired during the procession of the correction, with each comparison of strut lengths to planned strut lengths being based on the most recently updated correction plan (or on the original correction plan if not update has been performed).

It should further be noted that an application on detection device 200 may include other features relevant to the correction procedure. For example, with the correction plan stored in memory 210, the user may access the correction plan via detection device 200 so that the correction schedule may be conveniently stored. Because the correction schedule has a plurality of discrete corrections at specified time intervals, the application may include audible and/or visible signals or alarms at the relevant time intervals to remind the patient that a strut length adjustment is to be completed. The application may also provide helpful information, such as an indication of visual indicia corresponding to the different struts to be adjusted so that the patient may more easily confirm that he or she is adjusting the correct strut according to the correction plan. Further, any pictures taken via detection device 200 or otherwise transmitted to computer system 300 may be viewed by the physician to provide additional checks on whether the correction appears to be proceeding according to schedule.

Furthermore, as noted above, the patient may utilize a driver to adjust the length of each strut 130 during the correction procedure. In some cases, the driver may take the form of one or more "smart tools," such as those described in U.S. patent application Ser. No. 14/523,150, the disclosure of which is hereby incorporated by reference herein. In such smart tools, the driver may include a processor, memory, and communications module so that the smart tool may communicate with detection device 200 and/or computer system 300. With this capability, updated correction plans may be provided to, and stored within, the smart tool memory. During any particular strut length adjustment, the smart tool may access the most recent correction plan so that adjustment of the strut length occurs according to the correction plan. This feature may be particularly effective when the smart tool includes an electronic motor controlled by the processor in the smart tool, so that the amount of strut length adjustment may be precisely controlled.

Further, detection device 200 may be used as a correction plan tracker for the duration of the correction. This may be particularly useful if detection device 200 is a mobile device onto which an application may be installed. For example, the device 200, or an application installed on device 200, may provide information about the time each strut 130 should be actuated (i.e. changed in length) and the degree to which each strut 130 should be actuated at each scheduled correction. At, or prior to, each scheduled correction, device 200 may sound or otherwise provide an alarm to the user as a reminder. This may eliminate the need to have a paper schedule. Further, the patient may indicate on the device 200, for example by tapping a button on a touchscreen of the device 200, after every strut 130 correction is performed. This feature may be able to sync with a cloud system and/or computer 300 so that the physician (or hospital staff) can monitor the progress of the correction.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, features of one embodiment may be combined with features of other embodiments described herein.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A computer system including at least one processor configured to execute instructions to:
   receive a plurality of images of an external fixation system coupled to a patient, each image containing at least one strut of the external fixation system;
   determine a length of the at least one strut in each image;
   identify the at least one strut in each image corresponding to a predefined correction plan for the at least one strut in each image;
   compare the determined length of the at least one strut in each image to a planned strut length of the predefined correction plan, the planned strut lengths being stored in memory of the computer system;
   update the predefined correction plan to an updated correction plan to account for differences between the determined length and the planned strut length, the updated correction plan and the predefined correction plan having the same final configuration of the external fixation system;
   transmit the updated correction plan for adjusting the struts of the external fixation system.

2. The computer system of claim 1, wherein the instructions to identify the at least one strut in each image comprise comparing visual indicia on the at least one strut to corresponding indicia stored in the memory.

3. The computer system of claim 2, wherein the visual indicia is a quick response (QR) code.

4. The computer system of claim 1, wherein the planned strut lengths stored in memory include a length component and a time-interval component.

5. The computer system of claim 4, wherein the at least one processor is further configured to execute instructions to receive a time indicator corresponding to each of the plurality of images.

6. The computer system of claim 5, wherein the instructions to compare the determined length of each of the plurality of struts to the planned strut length further include comparing the time indicator corresponding to each of the plurality of images to a time-interval component of the planned strut length.

7. A computer system including at least one processor configured to execute instructions to:
   receive a plurality of images of an external fixation system coupled to a patient, each image containing at least one strut of the external fixation system;
   determine a length and an identity of the at least one strut in each image;
   compare the determined length of each of the plurality of struts to a corresponding planned strut length, the corresponding planned strut lengths being stored in an original correction plan in memory of the computer system;

update the original correction plan to an updated correction plan to account for differences between the determined length and the planned strut length, the updated correction plan and the original correction plan having the same final configuration of the external fixation system; and transmit the updated correction plan for adjusting the struts of the external fixation system.

8. The computer system of claim 7, wherein the instructions to determine the identity of the at least one strut in each image comprise comparing visual indicia on the at least one strut to corresponding indicia stored in the memory.

9. The computer system of claim 8, wherein the visual indicia is a quick response (QR) code.

10. The computer system of claim 7, wherein the corresponding planned strut lengths stored in memory include a length component and a time-interval component.

11. The computer system of claim 10, wherein the at least one processor is further configured to execute instructions to receive a time indicator corresponding to each of the plurality of images.

12. The computer system of claim 11, wherein the instructions to compare the determined length of each of the plurality of struts to a corresponding planned strut length further include comparing the time indicator corresponding to each of the plurality of images to a time-interval component of the planned strut lengths.

13. A computer system including at least one processor configured to execute instructions to:
determine a predefined correction for an external fixation system including a plurality of adjustable length struts, the predefined correction plan including for each of the plurality of adjustable length struts an original length and a final length;
receive a plurality of images of the external fixation system coupled to a patient, each image containing at least one strut of the external fixation system;
determine a length of the at least one strut in each image;
identify the at least one strut in each image corresponding to a time-interval in the predefined correction plan for the at least one strut in each image;
compare the determined length of the at least one strut in each image to a planned strut length at the time-interval in the predefined correction plan, the planned strut lengths being stored in memory of the computer system; and
update the predefined correction plan to an updated correction plan to account for differences between the determined length and the planned strut length, the updated correction plan and the predefined correction plan having the same final configuration of the external fixation system; and
transmit the updated correction plan for adjusting the struts of the external fixation system.

14. The computer system of claim 13, wherein the instructions to identify the at least one strut in each image comprise comparing visual indicia on the at least one strut to corresponding indicia stored in the memory.

15. The computer system of claim 14, wherein the visual indicia is a quick response (QR) code.

16. The computer system of claim 13, wherein the planned strut lengths stored in memory include a length component.

17. The computer system of claim 16, wherein the at least one processor is further configured to execute instructions to receive a time indicator corresponding to each of the plurality of images.

18. The computer system of claim 17, wherein the instructions to compare the determined length of each of the plurality of struts to the planned strut length further include comparing the time indicator corresponding to each of the plurality of images to the time-interval component of the planned strut length.

* * * * *